United States Patent
Debreczeny et al.

(10) Patent No.: US 8,062,221 B2
(45) Date of Patent: Nov. 22, 2011

(54) SENSOR FOR TISSUE GAS DETECTION AND TECHNIQUE FOR USING THE SAME

(75) Inventors: Martin P. Debreczeny, Danville, CA (US); Joel Colburn, Walnut Creek, CA (US); Michael P. O'Neil, Pleasanton, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1802 days.

(21) Appl. No.: 11/241,842

(22) Filed: Sep. 30, 2005

(65) Prior Publication Data

US 2007/0078307 A1    Apr. 5, 2007

(51) Int. Cl.
*A61B 5/00* (2006.01)
(52) U.S. Cl. ..... 600/309; 600/345; 600/353; 422/82.01; 422/82.05
(58) Field of Classification Search ................... 600/534, 600/364, 353; 128/207.14; 422/82.05
See application file for complete search history.

(56) References Cited

U.S. PATENT DOCUMENTS

| | | | |
|---|---|---|---|
| 2,136,236 A | 11/1938 | Drper | |
| 2,638,096 A | 5/1953 | Wldhus | |
| 2,880,072 A | 3/1959 | Grosskopf | |
| 2,890,177 A | 6/1959 | Kilmer | |
| 2,904,033 A | 9/1959 | Shne | |
| 3,067,015 A | 12/1962 | Lwdermilt | |
| 3,068,073 A | 12/1962 | Stnford | |
| 3,113,842 A | 12/1963 | Udll | |
| 3,114,610 A | 12/1963 | Gafford et al. | |
| 3,238,020 A | 3/1966 | Eisemn | |
| 3,363,833 A | 1/1968 | Lerdl | |
| 3,373,735 A | 3/1968 | Gllgher | |
| 3,420,635 A | 1/1969 | Dvis | |
| 3,467,601 A | 9/1969 | Bruer | |
| 3,505,022 A | 4/1970 | Luckey | |
| 3,507,623 A | 4/1970 | McConnughey | |
| 3,556,122 A | 1/1971 | Laerdal | |
| 3,612,048 A | 10/1971 | Takaoka | |
| 3,615,233 A | 10/1971 | Doering et al. | |
| 3,659,586 A | 5/1972 | Johns et al. | |
| 3,694,164 A | 9/1972 | Guenther | |
| 3,721,813 A | 3/1973 | Condon et al. | |
| 3,754,867 A | 8/1973 | Guenther | |
| 3,830,630 A | 8/1974 | Kiefer et al. | |
| 4,003,709 A | 1/1977 | Eaton et al. | |
| 4,019,862 A | 4/1977 | Dahms | |

(Continued)

FOREIGN PATENT DOCUMENTS

DE    1007525    5/1957

(Continued)

OTHER PUBLICATIONS

J.A. Berman et al.; "The Einstein Carbon Dioxide Detector"; Anesthesiology, vol. 60, No. 6; pp. 613-614 (1984).

(Continued)

*Primary Examiner* — Patricia Mallari
*Assistant Examiner* — Michael D'Angelo
(74) *Attorney, Agent, or Firm* — Fletcher Yoder

(57) ABSTRACT

A sensor for carbon dioxide detection may be adapted to have reduced water permeability. A sensor is provided that is appropriate for use in an aqueous medium. The sensor has a barrier with reduced water permeability, but that is permeable to carbon dioxide, that separates the sensor components from the aqueous medium.

29 Claims, 4 Drawing Sheets

U.S. PATENT DOCUMENTS

| | | | |
|---|---|---|---|
| 4,077,404 A | 3/1978 | Elam | |
| 4,106,502 A | 8/1978 | Wilson | |
| 4,144,306 A | 3/1979 | Figueras | |
| 4,277,251 A | 7/1981 | Leichnitz | |
| 4,287,153 A | 9/1981 | Towsend | |
| 4,332,771 A | 6/1982 | Leichnitz | |
| 4,346,584 A | 8/1982 | Boehringer | |
| 4,366,821 A | 1/1983 | Wittmaier et al. | |
| 4,389,372 A | 6/1983 | Lalin | |
| 4,438,067 A | 3/1984 | Siddiqi | |
| 4,548,906 A | 10/1985 | Sekikawa | |
| 4,557,900 A | 12/1985 | Heitzmann | |
| 4,557,901 A | 12/1985 | Koyama et al. | |
| 4,586,513 A | 5/1986 | Hamaguri | |
| 4,603,700 A | 8/1986 | Nichols et al. | |
| 4,621,643 A | 11/1986 | New, Jr. et al. | |
| 4,653,498 A | 3/1987 | New, Jr. et al. | |
| 4,685,464 A | 8/1987 | Goldberger et al. | |
| 4,691,701 A | 9/1987 | Williams | |
| 4,694,833 A | 9/1987 | Hamaguri | |
| 4,697,593 A | 10/1987 | Evans et al. | |
| 4,700,708 A | 10/1987 | New, Jr. et al. | |
| 4,714,080 A | 12/1987 | Edgar, Jr. et al. | |
| 4,714,341 A | 12/1987 | Hamaguri et al. | |
| 4,728,499 A | 3/1988 | Fehder | |
| 4,734,125 A | 3/1988 | Gehring et al. | |
| 4,759,369 A | 7/1988 | Taylor | |
| 4,770,179 A | 9/1988 | New, Jr. et al. | |
| 4,773,422 A | 9/1988 | Isaacson et al. | |
| 4,774,941 A | 10/1988 | Cook | |
| 4,776,339 A | 10/1988 | Schreiber | |
| 4,780,411 A | 10/1988 | Piejko et al. | |
| 4,781,195 A | 11/1988 | Martin | |
| 4,788,153 A | 11/1988 | Detwiler et al. | |
| 4,790,327 A | 12/1988 | Despotis | |
| 4,796,636 A | 1/1989 | Branstetter et al. | |
| 4,800,495 A | 1/1989 | Smith | |
| 4,800,885 A | 1/1989 | Johnson | |
| 4,802,486 A | 2/1989 | Goodman et al. | |
| 4,805,623 A | 2/1989 | Jöbsis | |
| 4,807,630 A | 2/1989 | Malinouskas | |
| 4,807,631 A | 2/1989 | Hersh et al. | |
| 4,819,646 A | 4/1989 | Cheung et al. | |
| 4,819,752 A | 4/1989 | Zelin | |
| 4,824,242 A | 4/1989 | Frick et al. | |
| 4,824,640 A | 4/1989 | Hildenbrand et al. | |
| 4,825,872 A | 5/1989 | Tan et al. | |
| 4,825,879 A | 5/1989 | Tan et al. | |
| 4,830,014 A | 5/1989 | Goodman et al. | |
| 4,832,484 A | 5/1989 | Aoyagi et al. | |
| 4,846,183 A | 7/1989 | Martin | |
| 4,848,901 A | 7/1989 | Hood, Jr. | |
| 4,854,699 A | 8/1989 | Edgar, Jr. | |
| 4,859,056 A | 8/1989 | Prosser et al. | |
| 4,859,057 A | 8/1989 | Taylor et al. | |
| 4,863,265 A | 9/1989 | Flower et al. | |
| 4,865,038 A | 9/1989 | Rich et al. | |
| 4,867,557 A | 9/1989 | Takatani et al. | |
| 4,869,253 A | 9/1989 | Craig, Jr. et al. | |
| 4,869,254 A | 9/1989 | Stone et al. | |
| 4,879,999 A | 11/1989 | Leiman et al. | |
| 4,880,304 A | 11/1989 | Jaeb et al. | |
| 4,883,055 A | 11/1989 | Merrick | |
| 4,883,353 A | 11/1989 | Hausman et al. | |
| 4,890,619 A | 1/1990 | Hatschek | |
| 4,892,101 A | 1/1990 | Cheung et al. | |
| 4,901,238 A | 2/1990 | Suzuki et al. | |
| 4,908,762 A | 3/1990 | Suzuki et al. | |
| 4,911,167 A | 3/1990 | Corenman et al. | |
| 4,913,150 A | 4/1990 | Cheung et al. | |
| 4,926,867 A | 5/1990 | Kanda et al. | |
| 4,927,264 A | 5/1990 | Shiga et al. | |
| 4,928,687 A | 5/1990 | Lampotang et al. | |
| 4,928,692 A | 5/1990 | Goodman et al. | |
| 4,934,372 A | 6/1990 | Corenman et al. | |
| 4,938,218 A | 7/1990 | Goodman et al. | |
| 4,942,877 A | 7/1990 | Sakai et al. | |
| 4,945,918 A | 8/1990 | Abernathy | |
| 4,948,248 A | 8/1990 | Lehman | |
| 4,955,379 A | 9/1990 | Hall | |
| 4,960,126 A | 10/1990 | Conlon et al. | |
| 4,964,408 A | 10/1990 | Hink et al. | |
| 4,971,062 A | 11/1990 | Hasebe et al. | |
| 4,974,591 A | 12/1990 | Awazu et al. | |
| 4,994,117 A | 2/1991 | Fehder | |
| 4,999,306 A | 3/1991 | Yafuso et al. | |
| 5,005,572 A * | 4/1991 | Raemer et al. | 128/207.14 |
| 5,007,423 A | 4/1991 | Branstetter et al. | |
| 5,025,791 A | 6/1991 | Niwa | |
| RE33,643 E | 7/1991 | Isaacson et al. | |
| 5,028,787 A | 7/1991 | Rosenthal et al. | |
| 5,035,243 A | 7/1991 | Muz | |
| 5,040,539 A | 8/1991 | Schmitt et al. | |
| 5,047,208 A * | 9/1991 | Schweitzer et al. | 422/58 |
| 5,054,488 A | 10/1991 | Muz | |
| 5,055,671 A | 10/1991 | Jones | |
| 5,058,588 A | 10/1991 | Kaestle | |
| 5,065,749 A | 11/1991 | Hasebe et al. | |
| 5,066,859 A | 11/1991 | Karkar et al. | |
| 5,069,213 A | 12/1991 | Polczynski | |
| 5,078,136 A | 1/1992 | Stone et al. | |
| 5,084,327 A | 1/1992 | Stengel | |
| 5,088,493 A | 2/1992 | Giannini et al. | |
| 5,090,410 A | 2/1992 | Saper et al. | |
| 5,094,239 A | 3/1992 | Jaeb et al. | |
| 5,094,240 A | 3/1992 | Muz | |
| 5,099,841 A | 3/1992 | Heinonen et al. | |
| 5,099,842 A | 3/1992 | Mannheimer et al. | |
| H1039 H | 4/1992 | Tripp, Jr. et al. | |
| 5,104,623 A | 4/1992 | Miller | |
| 5,109,840 A | 5/1992 | Daleiden | |
| 5,109,849 A | 5/1992 | Goodman et al. | |
| 5,111,817 A | 5/1992 | Clark et al. | |
| 5,113,861 A | 5/1992 | Rother | |
| 5,124,129 A | 6/1992 | Riccitelli et al. | |
| 5,125,403 A | 6/1992 | Culp | |
| 5,127,406 A | 7/1992 | Yamaguchi | |
| 5,131,391 A | 7/1992 | Sakai et al. | |
| 5,140,989 A | 8/1992 | Lewis et al. | |
| 5,152,296 A | 10/1992 | Simons | |
| 5,154,175 A | 10/1992 | Gunther | |
| 5,154,890 A * | 10/1992 | Mauze et al. | 422/82.07 |
| 5,156,159 A | 10/1992 | Lampotang et al. | |
| 5,158,082 A | 10/1992 | Jones | |
| 5,164,796 A | 11/1992 | Di Guiseppi et al. | |
| 5,166,075 A | 11/1992 | Fehder | |
| 5,170,786 A | 12/1992 | Thomas et al. | |
| 5,179,002 A | 1/1993 | Fehder | |
| 5,188,108 A | 2/1993 | Secker et al. | |
| 5,190,038 A | 3/1993 | Polson et al. | |
| 5,193,542 A | 3/1993 | Missanelli et al. | |
| 5,193,543 A | 3/1993 | Yelderman | |
| 5,197,464 A | 3/1993 | Babb et al. | |
| 5,203,329 A | 4/1993 | Takatani et al. | |
| 5,209,230 A | 5/1993 | Swedlow et al. | |
| 5,213,099 A | 5/1993 | Tripp et al. | |
| 5,216,598 A | 6/1993 | Branstetter et al. | |
| 5,217,012 A | 6/1993 | Young et al. | |
| 5,217,013 A | 6/1993 | Lewis et al. | |
| 5,218,962 A | 6/1993 | Mannheimer et al. | |
| 5,224,478 A | 7/1993 | Sakai et al. | |
| 5,226,417 A | 7/1993 | Swedlow et al. | |
| 5,228,440 A | 7/1993 | Chung et al. | |
| 5,237,994 A | 8/1993 | Goldberger | |
| 5,239,185 A | 8/1993 | Ito et al. | |
| 5,246,002 A | 9/1993 | Prosser | |
| 5,246,003 A | 9/1993 | DeLonzor | |
| 5,247,931 A | 9/1993 | Norwood | |
| 5,247,932 A | 9/1993 | Chung et al. | |
| 5,249,576 A | 10/1993 | Goldberger et al. | |
| 5,253,645 A | 10/1993 | Friedman et al. | |
| 5,253,646 A | 10/1993 | Delpy et al. | |
| 5,259,381 A | 11/1993 | Cheung et al. | |
| 5,259,761 A | 11/1993 | Schnettler et al. | |
| 5,263,244 A | 11/1993 | Centa et al. | |
| 5,267,562 A | 12/1993 | Ukawa et al. | |
| 5,267,563 A | 12/1993 | Swedlow et al. | |

| Patent | Date | Inventor |
|---|---|---|
| 5,273,036 A | 12/1993 | Kronberg et al. |
| 5,275,159 A | 1/1994 | Griebel |
| 5,279,289 A | 1/1994 | Kirk |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,879 A | 3/1994 | Babb et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,322,612 A | 6/1994 | Abe et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,372,136 A | 12/1994 | Steuer et al. |
| 5,375,592 A | 12/1994 | Kirk et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,456,249 A | 10/1995 | Kirk |
| 5,468,451 A | 11/1995 | Gedeon |
| 5,469,845 A | 11/1995 | DeLonzor et al. |
| RE35,122 E | 12/1995 | Corenman et al. |
| 5,472,668 A | 12/1995 | Mills et al. |
| 5,474,065 A | 12/1995 | Meathrel et al. |
| 5,480,611 A | 1/1996 | Mills et al. |
| 5,482,034 A | 1/1996 | Lewis et al. |
| 5,482,036 A | 1/1996 | Diab et al. |
| 5,483,646 A | 1/1996 | Uchikoga |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,494,640 A * | 2/1996 | Simon et al. ............... 422/82.05 |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,511,546 A | 4/1996 | Hon |
| 5,511,547 A | 4/1996 | Markle et al. |
| 5,517,985 A | 5/1996 | Kirk et al. |
| 5,517,988 A | 5/1996 | Gerhard |
| 5,520,177 A | 5/1996 | Ogawa et al. |
| 5,520,997 A | 5/1996 | Pourahmady et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz et al. |
| 5,538,620 A * | 7/1996 | Nikolskaja .................... 205/782 |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,595,176 A | 1/1997 | Yamaura |
| 5,596,986 A | 1/1997 | Goldfarb |
| 5,611,337 A | 3/1997 | Bukta |
| 5,617,852 A | 4/1997 | MacGregor |
| 5,619,992 A | 4/1997 | Guthrie et al. |
| 5,626,140 A | 5/1997 | Feldman et al. |
| 5,630,413 A | 5/1997 | Thomas et al. |
| 5,632,272 A | 5/1997 | Diab et al. |
| 5,632,273 A | 5/1997 | Suzuki |
| 5,634,426 A | 6/1997 | Tomlinson et al. |
| 5,634,459 A | 6/1997 | Gardosi |
| 5,638,593 A | 6/1997 | Gerhardt et al. |
| 5,638,818 A | 6/1997 | Diab et al. |
| 5,645,060 A | 7/1997 | Yorkey et al. |
| 5,645,440 A | 7/1997 | Tobler et al. |
| 5,660,567 A | 8/1997 | Nierlich et al. |
| 5,662,105 A | 9/1997 | Tien |
| 5,662,106 A | 9/1997 | Swedlow et al. |
| 5,666,952 A | 9/1997 | Fuse et al. |
| 5,671,529 A | 9/1997 | Nelson |
| 5,673,692 A | 10/1997 | Schulze et al. |
| 5,673,693 A | 10/1997 | Solenberger |
| 5,676,139 A | 10/1997 | Goldberger et al. |
| 5,676,141 A | 10/1997 | Hollub |
| 5,678,544 A | 10/1997 | DeLonzor et al. |
| 5,679,884 A | 10/1997 | Kirk |
| 5,680,857 A | 10/1997 | Pelikan et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,692,503 A | 12/1997 | Kuenstner |
| 5,692,505 A | 12/1997 | Fouts |
| 5,709,205 A | 1/1998 | Bukta |
| 5,713,355 A | 2/1998 | Richardson et al. |
| 5,714,121 A | 2/1998 | Alderete et al. |
| 5,724,967 A | 3/1998 | Venkatachalam |
| 5,727,547 A | 3/1998 | Levinson et al. |
| 5,731,582 A | 3/1998 | West |
| D393,830 S | 4/1998 | Tobler et al. |
| 5,743,260 A | 4/1998 | Chung et al. |
| 5,743,263 A | 4/1998 | Baker, Jr. |
| 5,746,206 A | 5/1998 | Mannheimer |
| 5,746,697 A | 5/1998 | Swedlow et al. |
| 5,749,358 A | 5/1998 | Good et al. |

| Patent | Date | Inventor | Patent | Date | Inventor |
|---|---|---|---|---|---|
| 5,752,914 A | 5/1998 | DeLonzor et al. | 5,924,980 A | 7/1999 | Coetzee |
| 5,755,226 A | 5/1998 | Carim et al. | 5,924,982 A | 7/1999 | Chin |
| 5,758,644 A | 6/1998 | Diab et al. | 5,924,985 A | 7/1999 | Jones |
| 5,760,910 A | 6/1998 | Lepper, Jr. et al. | 5,934,277 A | 8/1999 | Mortz |
| 5,766,125 A | 6/1998 | Aoyagi et al. | 5,934,925 A | 8/1999 | Tobler et al. |
| 5,766,127 A | 6/1998 | Pologe et al. | 5,940,182 A | 8/1999 | Lepper, Jr. et al. |
| 5,769,785 A | 6/1998 | Diab et al. | 5,954,644 A | 9/1999 | Dettling et al. |
| 5,772,587 A | 6/1998 | Gratton et al. | 5,960,610 A | 10/1999 | Levinson et al. |
| 5,774,213 A | 6/1998 | Trebino et al. | 5,961,450 A | 10/1999 | Merchant et al. |
| 5,776,058 A | 7/1998 | Levinson et al. | 5,961,452 A | 10/1999 | Chung et al. |
| 5,776,059 A | 7/1998 | Kaestle | 5,964,701 A | 10/1999 | Asada et al. |
| 5,779,630 A | 7/1998 | Fein et al. | 5,971,930 A | 10/1999 | Elghazzawi |
| 5,779,631 A | 7/1998 | Chance | 5,978,691 A | 11/1999 | Mills |
| 5,782,237 A | 7/1998 | Casciani et al. | 5,978,693 A | 11/1999 | Hamilton et al. |
| 5,782,756 A | 7/1998 | Mannheimer | 5,983,122 A | 11/1999 | Jarman et al. |
| 5,782,757 A | 7/1998 | Diab et al. | 5,987,343 A | 11/1999 | Kinast |
| 5,782,758 A | 7/1998 | Ausec et al. | 5,991,648 A | 11/1999 | Levin |
| 5,783,110 A | 7/1998 | Verdicchio et al. | 5,995,855 A | 11/1999 | Kiani et al. |
| 5,786,592 A | 7/1998 | Hök | 5,995,856 A | 11/1999 | Mannheimer et al. |
| 5,790,729 A | 8/1998 | Pologe et al. | 5,995,858 A | 11/1999 | Kinast |
| 5,792,052 A | 8/1998 | Isaacson et al. | 5,995,859 A | 11/1999 | Takahashi |
| 5,795,292 A | 8/1998 | Lewis et al. | 5,997,343 A | 12/1999 | Mills et al. |
| 5,797,841 A | 8/1998 | DeLonzor et al. | 5,999,834 A | 12/1999 | Wang et al. |
| 5,800,348 A | 9/1998 | Kaestle | 6,002,952 A | 12/1999 | Diab et al. |
| 5,800,349 A | 9/1998 | Isaacson et al. | 6,005,658 A | 12/1999 | Kaluza et al. |
| 5,803,910 A | 9/1998 | Potratz | 6,006,120 A | 12/1999 | Levin |
| 5,807,246 A | 9/1998 | Sakaguchi et al. | 6,011,985 A | 1/2000 | Athan et al. |
| 5,807,247 A | 9/1998 | Merchant et al. | 6,011,986 A | 1/2000 | Diab et al. |
| 5,807,248 A | 9/1998 | Mills | 6,014,576 A | 1/2000 | Raley et al. |
| 5,810,723 A | 9/1998 | Aldrich | 6,018,673 A | 1/2000 | Chin et al. |
| 5,810,724 A | 9/1998 | Gronvall | 6,018,674 A | 1/2000 | Aronow |
| 5,813,980 A | 9/1998 | Levinson et al. | 6,022,321 A | 2/2000 | Amano et al. |
| 5,817,008 A | 10/1998 | Rafert et al. | 6,023,541 A | 2/2000 | Merchant et al. |
| 5,817,009 A | 10/1998 | Rosenheimer et al. | 6,026,312 A | 2/2000 | Shemwell et al. |
| 5,817,010 A | 10/1998 | Hibl | 6,026,314 A | 2/2000 | Amerov et al. |
| 5,818,985 A | 10/1998 | Merchant et al. | 6,031,603 A | 2/2000 | Fine et al. |
| 5,820,550 A | 10/1998 | Polson et al. | 6,035,223 A | 3/2000 | Baker, Jr. |
| 5,823,950 A | 10/1998 | Diab et al. | 6,036,642 A | 3/2000 | Diab et al. |
| 5,823,952 A | 10/1998 | Levinson et al. | 6,041,247 A | 3/2000 | Weckstrom et al. |
| 5,827,182 A | 10/1998 | Raley et al. | 6,044,283 A | 3/2000 | Fein et al. |
| 5,830,135 A | 11/1998 | Bosque et al. | 6,047,201 A | 4/2000 | Jackson, III |
| 5,830,136 A | 11/1998 | DeLonzor et al. | 6,055,447 A * | 4/2000 | Weil et al. ............. 600/353 |
| 5,830,137 A | 11/1998 | Scharf | 6,058,933 A | 5/2000 | Good et al. |
| 5,839,439 A | 11/1998 | Nierlich et al. | 6,061,584 A | 5/2000 | Lovejoy et al. |
| RE36,000 E | 12/1998 | Swedlow et al. | 6,064,898 A | 5/2000 | Aldrich |
| 5,842,979 A | 12/1998 | Jarman et al. | 6,064,899 A | 5/2000 | Fein et al. |
| 5,842,981 A | 12/1998 | Larsen et al. | 6,067,462 A | 5/2000 | Diab et al. |
| 5,842,982 A | 12/1998 | Mannheimer | 6,073,038 A | 6/2000 | Wang et al. |
| 5,846,190 A | 12/1998 | Woehrle | 6,078,833 A | 6/2000 | Hueber |
| 5,846,836 A | 12/1998 | Mallow | 6,081,735 A | 6/2000 | Diab et al. |
| 5,849,594 A | 12/1998 | Balderson et al. | 6,081,742 A | 6/2000 | Amano et al. |
| 5,851,178 A | 12/1998 | Aronow | 6,083,157 A | 7/2000 | Noller |
| 5,851,179 A | 12/1998 | Ritson et al. | 6,083,172 A | 7/2000 | Baker, Jr. et al. |
| 5,853,364 A | 12/1998 | Baker, Jr. et al. | 6,088,607 A | 7/2000 | Diab et al. |
| 5,860,919 A | 1/1999 | Kiani-Azarbayjany et al. | 6,094,592 A | 7/2000 | Yorkey et al. |
| 5,865,736 A | 2/1999 | Baker, Jr. et al. | 6,095,974 A | 8/2000 | Shemwell et al. |
| 5,871,442 A | 2/1999 | Madarasz et al. | 6,104,938 A | 8/2000 | Huiku et al. |
| 5,879,294 A | 3/1999 | Anderson et al. | 6,112,107 A | 8/2000 | Hannula |
| 5,882,936 A | 3/1999 | Bentsen et al. | 6,113,541 A | 9/2000 | Dias et al. |
| 5,885,213 A | 3/1999 | Richardson et al. | 6,115,621 A | 9/2000 | Chin |
| 5,890,929 A | 4/1999 | Mills et al. | 6,122,535 A | 9/2000 | Kaestle et al. |
| 5,891,021 A | 4/1999 | Dillon et al. | 6,123,075 A | 9/2000 | Kirk |
| 5,891,022 A | 4/1999 | Pologe | 6,133,994 A | 10/2000 | Mathews et al. |
| 5,891,024 A | 4/1999 | Jarman et al. | 6,135,952 A | 10/2000 | Coetzee |
| 5,891,025 A | 4/1999 | Buschmann et al. | 6,144,444 A | 11/2000 | Haworth et al. |
| 5,891,026 A | 4/1999 | Wang et al. | 6,144,867 A | 11/2000 | Walker et al. |
| 5,902,235 A | 5/1999 | Lewis et al. | 6,144,868 A | 11/2000 | Parker |
| 5,910,108 A | 6/1999 | Solenberger | 6,149,481 A | 11/2000 | Wang et al. |
| 5,911,690 A | 6/1999 | Rall | 6,150,951 A | 11/2000 | Olejniczak |
| 5,912,656 A | 6/1999 | Tham et al. | 6,151,107 A | 11/2000 | Schöllerman et al. |
| 5,913,819 A | 6/1999 | Taylor et al. | 6,151,518 A | 11/2000 | Hayashi |
| 5,916,154 A | 6/1999 | Hobbs et al. | 6,152,754 A | 11/2000 | Gerhardt et al. |
| 5,916,155 A | 6/1999 | Levinson et al. | 6,154,667 A | 11/2000 | Miura et al. |
| 5,919,133 A | 7/1999 | Taylor et al. | 6,157,850 A | 12/2000 | Diab et al. |
| 5,919,134 A | 7/1999 | Diab | 6,163,175 A | 12/2000 | Sharpe-Geisler |
| 5,920,263 A | 7/1999 | Huttenhoff et al. | 6,163,715 A | 12/2000 | Larsen et al. |
| 5,921,921 A | 7/1999 | Potratz et al. | 6,165,005 A | 12/2000 | Mills et al. |
| 5,922,607 A | 7/1999 | Bernreuter | 6,173,196 B1 | 1/2001 | Delonzor et al. |
| 5,924,979 A | 7/1999 | Swedlow et al. | 6,178,343 B1 | 1/2001 | Bindszus et al. |

| | | |
|---|---|---|
| 6,181,958 B1 | 1/2001 | Steuer et al. |
| 6,181,959 B1 | 1/2001 | Schöllerman et al. |
| 6,184,521 B1 | 2/2001 | Coffin, IV et al. |
| 6,188,470 B1 | 2/2001 | Grace |
| 6,192,260 B1 | 2/2001 | Chance |
| 6,195,575 B1 | 2/2001 | Levinson |
| 6,198,951 B1 | 3/2001 | Kosuda et al. |
| 6,206,830 B1 | 3/2001 | Diab et al. |
| 6,213,952 B1 | 4/2001 | Finarov et al. |
| 6,216,024 B1 | 4/2001 | Weil et al. |
| 6,217,523 B1 | 4/2001 | Amano et al. |
| 6,222,189 B1 | 4/2001 | Misner et al. |
| 6,226,539 B1 | 5/2001 | Potratz |
| 6,226,540 B1 | 5/2001 | Bernreuter et al. |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grimblatov |
| 6,263,221 B1 | 7/2001 | Chance et al. |
| 6,263,222 B1 | 7/2001 | Diab et al. |
| 6,263,223 B1 | 7/2001 | Sheperd et al. |
| 6,265,221 B1 | 7/2001 | Nilsson |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,807 B1 * | 9/2001 | Walt et al. ............... 385/12 |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,319,723 B1 | 11/2001 | Jeffers et al. |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura et al. |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| 6,370,408 B1 | 4/2002 | Merchant et al. |
| 6,370,409 B1 | 4/2002 | Chung et al. |
| 6,374,129 B1 | 4/2002 | Chin et al. |
| 6,377,829 B1 | 4/2002 | Al-Ali et al. |
| 6,378,522 B1 | 4/2002 | Pagan |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenster |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,419,671 B1 | 7/2002 | Lemberg |
| 6,421,549 B1 | 7/2002 | Jacques |
| 6,427,687 B1 | 8/2002 | Kirk |
| 6,428,748 B1 | 8/2002 | Wallach |
| 6,430,423 B1 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,436,347 B1 | 8/2002 | Cedeon |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,502,573 B1 | 1/2003 | Ratner |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,576,474 B2 | 6/2003 | Wallach |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| D478,522 S | 8/2003 | Geist |
| 6,606,510 B2 | 8/2003 | Swedlow et al. |
| 6,606,511 B1 | 8/2003 | Ali et al. |
| 6,606,512 B2 | 8/2003 | Muz et al. |
| 6,615,064 B1 | 9/2003 | Aldrich |
| 6,615,065 B1 | 9/2003 | Barrett et al. |
| 6,618,602 B1 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |

| | | | |
|---|---|---|---|
| 6,650,917 B2 | 11/2003 | Diab et al. | |
| 6,650,918 B2 | 11/2003 | Terry | |
| 6,654,621 B2 | 11/2003 | Palatnik et al. | |
| 6,654,622 B1 | 11/2003 | Eberhard et al. | |
| 6,654,623 B1 | 11/2003 | Kästle | |
| 6,654,624 B2 | 11/2003 | Diab et al. | |
| 6,658,276 B2 | 12/2003 | Pishney et al. | |
| 6,658,277 B2 | 12/2003 | Wassermann | |
| 6,662,033 B2 | 12/2003 | Casciani et al. | |
| 6,665,551 B1 | 12/2003 | Suzuki | |
| 6,668,182 B2 | 12/2003 | Hubelbank | |
| 6,668,183 B2 | 12/2003 | Hicks et al. | |
| 6,671,526 B1 | 12/2003 | Aoyagi et al. | |
| 6,671,528 B2 | 12/2003 | Steuer et al. | |
| 6,671,530 B2 | 12/2003 | Chung et al. | |
| 6,671,531 B2 | 12/2003 | Al-Ali et al. | |
| 6,671,532 B1 | 12/2003 | Fudge et al. | |
| 6,675,031 B1 | 1/2004 | Porges et al. | |
| 6,677,159 B1 | 1/2004 | Mallow | |
| 6,678,543 B2 | 1/2004 | Diab et al. | |
| 6,681,126 B2 | 1/2004 | Solenberger | |
| 6,681,128 B2 | 1/2004 | Steuer et al. | |
| 6,681,454 B2 | 1/2004 | Modgil et al. | |
| 6,684,090 B2 | 1/2004 | Ali et al. | |
| 6,684,091 B2 | 1/2004 | Parker | |
| 6,694,160 B2 | 2/2004 | Chin | |
| 6,697,653 B2 | 2/2004 | Hanna | |
| 6,697,655 B2 | 2/2004 | Sueppel et al. | |
| 6,697,656 B1 | 2/2004 | Al-Ali | |
| 6,697,658 B2 | 2/2004 | Al-Ali | |
| RE38,476 E | 3/2004 | Diab et al. | |
| 6,699,194 B1 | 3/2004 | Diab et al. | |
| 6,699,199 B2 | 3/2004 | Asada et al. | |
| 6,701,170 B2 | 3/2004 | Stetson | |
| 6,702,752 B2 | 3/2004 | Dekker | |
| 6,707,257 B2 | 3/2004 | Norris | |
| 6,708,049 B1 | 3/2004 | Berson et al. | |
| 6,709,402 B2 | 3/2004 | Dekker | |
| 6,709,403 B1 | 3/2004 | Ratner | |
| 6,711,424 B1 | 3/2004 | Fine et al. | |
| 6,711,425 B1 | 3/2004 | Reuss | |
| 6,714,803 B1 | 3/2004 | Mortz | |
| 6,714,804 B2 | 3/2004 | Al-Ali et al. | |
| 6,714,805 B2 | 3/2004 | Jeon et al. | |
| RE38,492 E | 4/2004 | Diab et al. | |
| 6,719,686 B2 | 4/2004 | Coakley et al. | |
| 6,719,705 B2 | 4/2004 | Mills | |
| 6,720,734 B2 | 4/2004 | Norris | |
| 6,721,584 B2 | 4/2004 | Baker, Jr. et al. | |
| 6,721,585 B1 | 4/2004 | Parker | |
| 6,723,077 B2 | 4/2004 | Pickup et al. | |
| 6,725,074 B1 | 4/2004 | Kästle | |
| 6,725,075 B2 | 4/2004 | Al-Ali | |
| 6,731,963 B2 | 5/2004 | Finarov et al. | |
| 6,731,967 B1 | 5/2004 | Turcott | |
| 6,735,459 B2 | 5/2004 | Parker | |
| 6,745,060 B2 | 6/2004 | Diab et al. | |
| 6,745,061 B1 | 6/2004 | Hicks et al. | |
| 6,748,253 B2 | 6/2004 | Norris et al. | |
| 6,748,254 B2 | 6/2004 | Chin et al. | |
| 6,754,515 B1 | 6/2004 | Pologe | |
| 6,754,516 B2 | 6/2004 | Mannheimer | |
| 6,760,607 B2 | 7/2004 | Al-All | |
| 6,760,609 B2 | 7/2004 | Jacques | |
| 6,760,610 B2 | 7/2004 | Tscupp et al. | |
| 6,763,255 B2 | 7/2004 | DeLonzor et al. | |
| 6,763,256 B2 | 7/2004 | Kimball et al. | |
| 6,770,028 B1 | 8/2004 | Ali et al. | |
| 6,771,994 B2 | 8/2004 | Kiani et al. | |
| 6,773,397 B2 | 8/2004 | Kelly | |
| 6,778,923 B2 | 8/2004 | Norris et al. | |
| 6,780,158 B2 | 8/2004 | Yarita | |
| 6,791,689 B1 | 9/2004 | Weckström | |
| 6,792,300 B1 | 9/2004 | Diab et al. | |
| 6,793,654 B2 | 9/2004 | Lemberg | |
| 6,801,797 B2 | 10/2004 | Mannheimer et al. | |
| 6,801,798 B2 | 10/2004 | Geddes et al. | |
| 6,801,799 B2 | 10/2004 | Mendelson | |
| 6,801,802 B2 | 10/2004 | Sitzman et al. | |
| 6,802,812 B1 | 10/2004 | Walker et al. | |
| 6,805,673 B2 | 10/2004 | Dekker | |
| 6,810,277 B2 | 10/2004 | Edgar, Jr. et al. | |
| 6,813,511 B2 | 11/2004 | Diab et al. | |
| 6,816,741 B2 | 11/2004 | Diab | |
| 6,819,950 B2 | 11/2004 | Mills | |
| 6,825,619 B2 | 11/2004 | Norris | |
| 6,826,419 B2 | 11/2004 | Diab et al. | |
| 6,829,496 B2 | 12/2004 | Nagai et al. | |
| 6,830,711 B2 | 12/2004 | Mills et al. | |
| 6,836,679 B2 | 12/2004 | Baker, Jr. et al. | |
| 6,839,579 B1 | 1/2005 | Chin | |
| 6,839,580 B2 | 1/2005 | Zonios et al. | |
| 6,839,582 B2 | 1/2005 | Heckel | |
| 6,839,659 B2 | 1/2005 | Tarassenko et al. | |
| 6,842,635 B1 | 1/2005 | Parker | |
| 6,845,256 B2 | 1/2005 | Chin et al. | |
| 6,850,787 B2 | 2/2005 | Weber et al. | |
| 6,850,788 B2 | 2/2005 | Al-Ali | |
| 6,850,789 B2 | 2/2005 | Schweitzer, Jr. et al. | |
| 6,861,639 B2 | 3/2005 | Al-Ali | |
| 6,863,652 B2 | 3/2005 | Huang et al. | |
| 6,865,407 B2 | 3/2005 | Kimball et al. | |
| 6,879,850 B2 | 4/2005 | Kimball | |
| 6,882,874 B2 | 4/2005 | Huiku | |
| 6,889,153 B2 | 5/2005 | Dietiker | |
| 6,898,452 B2 | 5/2005 | Al-Ali et al. | |
| 6,909,912 B2 | 6/2005 | Melker et al. | |
| 6,912,413 B2 | 6/2005 | Rantala et al. | |
| 6,916,289 B2 | 7/2005 | Schnall | |
| 6,920,345 B2 | 7/2005 | Al-Ali et al. | |
| 6,929,008 B2 | 8/2005 | Geist | |
| 6,931,269 B2 | 8/2005 | Terry | |
| 6,934,570 B2 | 8/2005 | Kiani et al. | |
| 6,939,307 B1 | 9/2005 | Dunlop | |
| 6,941,162 B2 | 9/2005 | Fudge et al. | |
| 6,947,781 B2 | 9/2005 | Asada et al. | |
| 6,950,687 B2 | 9/2005 | Al-Ali | |
| 6,963,767 B2 | 11/2005 | Rantala et al. | |
| 6,971,580 B2 | 12/2005 | Zhu et al. | |
| 6,983,178 B2 | 1/2006 | Fine et al. | |
| 6,985,763 B2 | 1/2006 | Boas et al. | |
| 6,985,764 B2 | 1/2006 | Mason et al. | |
| 6,990,426 B2 | 1/2006 | Yoon et al. | |
| 6,992,751 B2 | 1/2006 | Okita et al. | |
| 6,992,772 B2 | 1/2006 | Block et al. | |
| 6,993,371 B2 | 1/2006 | Kiani et al. | |
| 6,993,372 B2 | 1/2006 | Fine et al. | |
| 6,996,427 B2 | 2/2006 | Ali et al. | |
| 7,003,338 B2 | 2/2006 | Weber et al. | |
| 7,003,339 B2 | 2/2006 | Diab et al. | |
| 7,006,855 B1 | 2/2006 | Sarussi | |
| 7,006,856 B2 | 2/2006 | Baker, Jr. et al. | |
| 7,016,715 B2 | 3/2006 | Stetson | |
| 7,020,507 B2 | 3/2006 | Scharf et al. | |
| 7,024,233 B2 | 4/2006 | Ali et al. | |
| 7,024,235 B2 | 4/2006 | Melker et al. | |
| 7,025,728 B2 | 4/2006 | Ito et al. | |
| 7,027,849 B2 | 4/2006 | Al-Ali et al. | |
| 7,027,850 B2 | 4/2006 | Wasserman | |
| 7,035,697 B1 | 4/2006 | Brown | |
| 7,039,449 B2 | 5/2006 | Al-Ali | |
| 7,043,289 B2 | 5/2006 | Fine et al. | |
| 7,047,055 B2 | 5/2006 | Boaz et al. | |
| 7,047,056 B2 | 5/2006 | Hannula et al. | |
| 7,060,035 B2 | 6/2006 | Wasserman et al. | |
| 7,062,307 B2 | 6/2006 | Norris et al. | |
| 7,067,893 B2 | 6/2006 | Mills et al. | |
| 7,072,701 B2 | 7/2006 | Chen et al. | |
| 7,072,702 B2 | 7/2006 | Edgar, Jr. et al. | |
| 7,079,880 B2 | 7/2006 | Stetson | |
| 7,085,597 B2 | 8/2006 | Fein et al. | |
| 7,096,052 B2 | 8/2006 | Mason et al. | |
| 7,096,054 B2 | 8/2006 | Adbul-Hafiz et al. | |
| 7,107,088 B2 | 9/2006 | Aceti | |
| 7,113,815 B2 | 9/2006 | O'Neil et al. | |
| 7,123,950 B2 | 10/2006 | Mannheimer | |
| 7,127,278 B2 | 10/2006 | Melker et al. | |
| 7,130,671 B2 | 10/2006 | Baker, Jr. et al. | |

| | | | | | |
|---|---|---|---|---|---|
| 7,132,641 B2 | 11/2006 | Schulz et al. | 2004/0116788 A1 | 6/2004 | Chernoguz et al. |
| 7,133,711 B2 | 11/2006 | Chernoguz et al. | 2004/0116789 A1 | 6/2004 | Boaz et al. |
| 7,139,599 B2 | 11/2006 | Terry | 2004/0117891 A1 | 6/2004 | Hannula et al. |
| 7,142,901 B2 | 11/2006 | Kiani et al. | 2004/0122300 A1 | 6/2004 | Boas et al. |
| 7,162,288 B2 | 1/2007 | Nordstrom | 2004/0122302 A1 | 6/2004 | Mason et al. |
| 7,190,987 B2 | 3/2007 | Lindekugel et al. | 2004/0133087 A1 | 7/2004 | Ali et al. |
| 7,198,778 B2 | 4/2007 | Achilefu et al. | 2004/0133088 A1 | 7/2004 | Al-Ali et al. |
| 7,209,775 B2 | 4/2007 | Bae et al. | 2004/0138538 A1 | 7/2004 | Stetson |
| 7,215,984 B2 | 5/2007 | Diab et al. | 2004/0138540 A1 | 7/2004 | Baker, Jr. et al. |
| 7,225,006 B2 | 5/2007 | Al-Ali et al. | 2004/0143172 A1 | 7/2004 | Fudge et al. |
| 7,225,007 B2 | 5/2007 | Al-Ali et al. | 2004/0147821 A1 | 7/2004 | Al-Ali et al. |
| 7,236,811 B2 | 6/2007 | Schmitt | 2004/0147822 A1 | 7/2004 | Al-Ali et al. |
| 7,236,881 B2 | 6/2007 | Liu et al. | 2004/0147823 A1 | 7/2004 | Kiani et al. |
| 7,248,910 B2 | 7/2007 | Li et al. | 2004/0147824 A1 | 7/2004 | Diab et al. |
| 7,254,433 B2 | 8/2007 | Diab et al. | 2004/0152965 A1 | 8/2004 | Diab et al. |
| 7,254,434 B2 | 8/2007 | Schulz et al. | 2004/0158134 A1 | 8/2004 | Diab et al. |
| 7,263,395 B2 | 8/2007 | Chan et al. | 2004/0158135 A1 | 8/2004 | Baker, Jr. et al. |
| 7,272,426 B2 | 9/2007 | Scmid | 2004/0162472 A1 | 8/2004 | Berson et al. |
| 7,280,858 B2 | 10/2007 | Al-Ali et al. | 2004/0171920 A1 | 9/2004 | Mannheimer et al. |
| 7,295,866 B2 | 11/2007 | Al-Ali et al. | 2004/0171948 A1 | 9/2004 | Terry |
| 7,305,262 B2 | 12/2007 | Brodnick et al. | 2004/0176671 A1 | 9/2004 | Fine et al. |
| 7,315,753 B2 | 1/2008 | Baker, Jr. et al. | 2004/0181133 A1 | 9/2004 | Al-Ali et al. |
| 2001/0021803 A1 | 9/2001 | Blank et al. | 2004/0181134 A1 | 9/2004 | Baker, Jr. et al. |
| 2001/0051767 A1 | 12/2001 | Williams et al. | 2004/0181196 A1 | 9/2004 | Pickup et al. |
| 2002/0026109 A1 | 2/2002 | Diab et al. | 2004/0184024 A1 | 9/2004 | Katura et al. |
| 2002/0028990 A1 | 3/2002 | Sheperd et al. | 2004/0186358 A1 | 9/2004 | Chernow et al. |
| 2002/0038078 A1 | 3/2002 | Ito | 2004/0199063 A1 | 10/2004 | O'Neil et al. |
| 2002/0042558 A1 | 4/2002 | Mendelson | 2004/0204636 A1 | 10/2004 | Diab et al. |
| 2002/0068859 A1 | 6/2002 | Knopp | 2004/0204637 A1 | 10/2004 | Diab et al. |
| 2002/0128544 A1 | 9/2002 | Diab et al. | 2004/0204638 A1 | 10/2004 | Diab et al. |
| 2002/0133067 A1 | 9/2002 | Jackson, III | 2004/0204639 A1 | 10/2004 | Casciani et al. |
| 2002/0156354 A1 | 10/2002 | Larson | 2004/0204865 A1 | 10/2004 | Lee et al. |
| 2002/0173706 A1 | 11/2002 | Takatani | 2004/0210146 A1 | 10/2004 | Diab et al. |
| 2002/0173709 A1 | 11/2002 | Fine et al. | 2004/0215069 A1 | 10/2004 | Mannheimer |
| 2002/0190863 A1 | 12/2002 | Lynn | 2004/0230107 A1 | 11/2004 | Asada et al. |
| 2002/0198442 A1 | 12/2002 | Rantala et al. | 2004/0230108 A1 | 11/2004 | Melker et al. |
| 2003/0003593 A1 | 1/2003 | Wallach | 2004/0236196 A1 | 11/2004 | Diab et al. |
| 2003/0018243 A1 | 1/2003 | Gerhardt et al. | 2004/0242980 A1 | 12/2004 | Kiani et al. |
| 2003/0036690 A1 | 2/2003 | Geddes et al. | 2004/0249252 A1 | 12/2004 | Fine et al. |
| 2003/0045785 A1 | 3/2003 | Diab et al. | 2004/0257557 A1 | 12/2004 | Block et al. |
| 2003/0073889 A1 | 4/2003 | Keilbach et al. | 2004/0260161 A1 | 12/2004 | Melker et al. |
| 2003/0073890 A1 | 4/2003 | Hanna | 2004/0267103 A1 | 12/2004 | Li et al. |
| 2003/0100840 A1 | 5/2003 | Sugiura et al. | 2004/0267104 A1 | 12/2004 | Hannula et al. |
| 2003/0132495 A1 | 7/2003 | Mills et al. | 2004/0267140 A1 | 12/2004 | Ito et al. |
| 2003/0133123 A1 | 7/2003 | Yeh | 2005/0004479 A1 | 1/2005 | Townsend et al. |
| 2003/0135099 A1 | 7/2003 | Al-Ali | 2005/0010092 A1 | 1/2005 | Weber et al. |
| 2003/0162414 A1 | 8/2003 | Schulz et al. | 2005/0016543 A1 | 1/2005 | Geist |
| 2003/0171662 A1 | 9/2003 | O'Connor et al. | 2005/0020887 A1 | 1/2005 | Goldberg |
| 2003/0176776 A1 | 9/2003 | Huiku | 2005/0020894 A1 | 1/2005 | Norris et al. |
| 2003/0181799 A1 | 9/2003 | Lindekugel et al. | 2005/0033128 A1 | 2/2005 | Ali et al. |
| 2003/0187337 A1 | 10/2003 | Tarassenko et al. | 2005/0033129 A1 | 2/2005 | Edgar, Jr. et al. |
| 2003/0195402 A1 | 10/2003 | Fein et al. | 2005/0039751 A1 | 2/2005 | Pagan |
| 2003/0197679 A1 | 10/2003 | Ali et al. | 2005/0043599 A1 | 2/2005 | O'Mara |
| 2003/0199095 A1 | 10/2003 | Yuyama et al. | 2005/0043600 A1 | 2/2005 | Diab et al. |
| 2003/0212316 A1 | 11/2003 | Leiden et al. | 2005/0049470 A1 | 3/2005 | Terry |
| 2003/0225323 A1 | 12/2003 | Kiani et al. | 2005/0049471 A1 | 3/2005 | Aceti |
| 2003/0225337 A1 | 12/2003 | Scharf et al. | 2005/0075550 A1 | 4/2005 | Lindekugel |
| 2003/0236452 A1 | 12/2003 | Melker et al. | 2005/0113651 A1 | 5/2005 | Wood et al. |
| 2003/0236647 A1 | 12/2003 | Yoon et al. | 2005/0177034 A1 | 8/2005 | Beaumont |
| 2004/0006261 A1 | 1/2004 | Swedlow et al. | 2005/0197548 A1 | 9/2005 | Dietiker |
| 2004/0010188 A1 | 1/2004 | Wasserman et al. | 2005/0228248 A1 | 10/2005 | Dietiker |
| 2004/0024297 A1 | 2/2004 | Chen et al. | 2005/0277819 A1 | 12/2005 | Kiani et al. |
| 2004/0024326 A1 | 2/2004 | Yeo et al. | 2006/0058594 A1 | 3/2006 | Ishizuka et al. |
| 2004/0034293 A1 | 2/2004 | Kimball | 2006/0084852 A1 | 4/2006 | Mason et al. |
| 2004/0039272 A1 | 2/2004 | Abdul-Hafiz et al. | 2006/0089547 A1 | 4/2006 | Sarussi |
| 2004/0039273 A1 | 2/2004 | Terry | 2006/0106294 A1 | 5/2006 | Maser et al. |
| 2004/0054269 A1 | 3/2004 | Rantala et al. | 2006/0195028 A1 | 8/2006 | Hannula et al. |
| 2004/0054291 A1 | 3/2004 | Schulz et al. | 2006/0224058 A1 | 10/2006 | Mannheimer |
| 2004/0059209 A1 | 3/2004 | Al-Ali et al. | 2006/0247501 A1 | 11/2006 | Ali |
| 2004/0059210 A1 | 3/2004 | Stetson | 2006/0258921 A1 | 11/2006 | Addison et al. |
| 2004/0064020 A1 | 4/2004 | Diab et al. | 2006/0276700 A1 | 12/2006 | O'Neil et al. |
| 2004/0065329 A1 | 4/2004 | Geist | 2007/0032710 A1 | 2/2007 | Raridan et al. |
| 2004/0068164 A1 | 4/2004 | Diab et al. | 2007/0032712 A1 | 2/2007 | Raridan et al. |
| 2004/0087846 A1 | 5/2004 | Wasserman | 2007/0032715 A1 | 2/2007 | Eghbal et al. |
| 2004/0087916 A1 | 5/2004 | Pickup et al. | 2007/0073121 A1 | 3/2007 | Hoarau et al. |
| 2004/0092805 A1 | 5/2004 | Yarita | 2007/0073125 A1 | 3/2007 | Hoarau et al. |
| 2004/0097797 A1 | 5/2004 | Porges et al. | 2007/0073126 A1 | 3/2007 | Raridan, Jr. |
| 2004/0098009 A1 | 5/2004 | Boecker et al. | 2007/0073128 A1 | 3/2007 | Hoarau et al. |
| 2004/0107065 A1 | 6/2004 | Al-Ali et al. | 2007/0244378 A1 | 10/2007 | Al-Ali et al. |

FOREIGN PATENT DOCUMENTS

| | | |
|---|---|---|
| EP | 0451719 | 10/1991 |
| EP | 0481719 | 4/1992 |
| EP | 1153294 | 4/1992 |
| EP | 0509998 | 10/1992 |
| EP | 0307625 | 4/1994 |
| EP | 0592632 | 4/1994 |
| EP | 0257916 | 1/1995 |
| EP | 1245947 | 3/1995 |
| EP | 1266944 | 6/1996 |
| EP | 1327874 | 9/1996 |
| EP | 01022558 | 7/2000 |
| EP | 0601171 | 10/2000 |
| EP | 0943093 | 10/2002 |
| EP | 1022558 | 12/2002 |
| EP | 1039294 | 7/2003 |
| EP | 0858594 | 10/2003 |
| GB | 1043988 | 12/1997 |
| JP | 09318528 | 7/1991 |
| JP | 10073560 | 12/1995 |
| JP | 2003072857 | 12/1998 |
| JP | 07072081 | 3/2003 |
| JP | 2004177247 | 3/2004 |
| JP | 2005054048 | 4/2004 |
| JP | 08145979 | 6/2004 |
| JP | 08247997 | 3/2005 |
| WO | WO90/01695 | 2/1990 |
| WO | WO90/03819 | 4/1990 |
| WO | WO91/05252 | 4/1991 |
| WO | WO92/20404 | 11/1992 |
| WO | WO 93/15402 | 8/1993 |
| WO | WO93/20431 | 10/1993 |
| WO | WO94/00756 | 1/1994 |
| WO | WO96/19727 | 6/1996 |
| WO | WO96/24054 | 8/1996 |
| WO | WO97/10496 | 3/1997 |
| WO | WO97/12227 | 4/1997 |
| WO | WO98/26283 | 6/1998 |
| WO | WO00/29830 | 5/2000 |
| WO | WO 00/29832 | 5/2000 |
| WO | WO00/43778 | 7/2000 |
| WO | WO01/04624 | 1/2001 |
| WO | WO01/44385 | 6/2001 |
| WO | WO2004/077035 | 9/2004 |
| WO | WO2005/065540 | 7/2005 |

OTHER PUBLICATIONS

P.K. Birmingham et al.; "Esophageal Intubation: A Review of Detection Techniques"; Anesth. Analg.; vol. 65; pp. 886-891 (1986).

Weil, Max Harry, et al.; "Sublingual Capnometry: A New Noninvasive Measurement for Diagnosis and Quantitation of Severity of Circulatory Shock"; Cirtical Care Medicine,vol. 27, No. 7 (1999).

Rohling, Roman, et al.; "Clinical Investigation of a New Combined Pulse Oximetry and Carbon Dioxide Tension Sensor in Adult Anaesthesia," *Journal of Clinical Monitoring and Computing*, vol. 15; pp. 23-27 (1999).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

S.G.R.G. Barton et al.; "Expression of heat shock protein 32 (hemoxygenase-1) in the normal and inflamed human stomach and colon: an immunohistochemical study"; Cell Stress & Chaperones, vol. 8, No. 4; pp. 329-334 (2003).

Kubota, H., et al.; "Simultaneous Monitoring of PtcCO2 and SpO2 using a Miniature earlobe sensor," *Jinko Kokyo (Aritificial Respiration)*, vol. 20, No. 1, pp. 24-29 (2003).

Kocher, Serge, et al.; "Performance of a Digital $PCO_2$/$SPO_2$ Ear Sensor," *Journal of Clinical Monitoring and Computing*, vol. 18, pp. 75-59 (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Jessy Deshane et al.; "Heme oxygenase-1 expression in disease states"; Acta Biochimica Polonica, vol. 52, No. 2; pp. 273-284 (2005).

Shai Efrati, MD et al.; "Optimization of Endotracheal Tube Cuff Filling by Continuous Upper Airway Carbon Dioxide Monitoring"; Anesth. Analg; vol. 101, pp. 1081-1088 (2005).

Shai Efrati, MD; "Is Capnometry the Optimum Method for Assessing the Adequacy of Endotracheal Tube Cuff Seal?"; Anesthesia & Analgesia; vol. 103, No. 2; pp. 505-506 (Aug. 2006).

Shaw-Fang Yet et al.; "Heme Oxygenase 1 in Regulation of Inflammation and Oxidative Damage"; Methods in Enzymology; vol. 353, pp. 163-176 (2002).

J. Hayoz, et al.; "World's First Combined digital Pulse Oximetry Pulse Oximetry and Carbon Dioxide Tension Ear Sensor", *Abstracts*, A6, p. S103. (undated).

\* cited by examiner

SENSOR FOR TISSUE GAS DETECTION AND TECHNIQUE FOR USING THE SAME

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

Among other blood constituents, physicians often desire to monitor levels of carbon dioxide in a patient's bloodstream. For example, decreased levels of carbon dioxide in the blood may be related to poor perfusion. Thus, assessment of carbon dioxide levels may be useful for diagnosing a variety of clinical states related to poor perfusion. One method of determining the level of blood carbon dioxide involves measuring carbon dioxide levels of respiratory gases. As carbon dioxide in the bloodstream equilibrates rapidly with carbon dioxide in the lungs, the partial pressure of the carbon dioxide in the lungs approaches the amount in the blood during each breath. Accordingly, physicians often monitor respiratory gases during breathing in order to estimate the carbon dioxide levels in the blood.

Respiratory gas analyzers typically function by passing electromagnetic radiation through a respiratory gas sample and measuring the absorption that is related to carbon dioxide. Often, the gas samples are collected with adapters that are fitted into patients being given respiratory assistance, such as patients under anesthesia or patients on life support systems, to connect between the endotracheal tube (ET tube) and the ventilating tube of the breathing apparatus. These tubes convey breathing gases to the patient and exhaled breath away from the patient. The airway adapter is in the form of a short connector of tubular shape, and the adapter is required to make a connection between the generally very different cross sections of these two tubes.

Respiratory gases may also be collected through the use of cannulas, which are flexible tubes that are threaded through the mouth or nose. Respiratory gas samples collected from a cannula may be aspirated from the airway stream and exposed to a carbon dioxide sensor.

It is often inconvenient to measure carbon dioxide in respiratory gases from respiratory gas samples collected from an intubation tube or cannula. Although these methods are considered to be noninvasive, as the surface of the skin is not breached, the insertion of such devices may cause discomfort for the patient. Further, the insertion and operation of such devices also involves the assistance of skilled medical personnel.

Carbon dioxide may also be measured transcutaneously by sensors held against a patient's skin. While these sensors are easier to use than respiratory gas sensors, they also have certain disadvantages. Because transcutaneous sensors depend upon the perfusion of carbon dioxide through a relatively thick epidermal layer, these sensors may not be as accurate. This problem may be addressed by measuring carbon dioxide that perfuses through a relatively thinner mucous membrane surface. However, a patient's mucous membrane is an aqueous environment, and surrounding water and other fluids may infiltrate a sensor, possibly damaging the sensing components and causing measurement inaccuracies.

Thus, it may be desirable to provide a water-resistant sensor for the measurement of carbon dioxide and other gases to protect a sensor that may be used in relatively aqueous environments, such as those containing mucous membranes.

SUMMARY

Certain aspects commensurate in scope with the originally claimed invention are set forth below. It should be understood that these aspects are presented merely to provide the reader with a brief summary of certain forms that the invention might take and that these aspects are not intended to limit the scope of the invention. Indeed, the invention may encompass a variety of aspects that may not be set forth below.

There is provided a sensor that includes: a solid indicator layer adapted to provide feedback related to a presence of carbon dioxide in a non-gaseous patient sample; and a selective barrier disposed on a sample-contacting side of the indicator, wherein the selective barrier is permeable to carbon dioxide and substantially impermeable to water.

There is also provided a system that includes a sensor adapted to be operatively coupled to the monitor. The sensor includes: a solid indicator layer adapted to provide feedback related to a presence of carbon dioxide in a non-gaseous patient sample; and a selective barrier disposed on a sample-contacting side of the indicator, wherein the selective barrier is permeable to carbon dioxide and substantially impermeable to water.

There is also provided a method of operating a sensor that includes: contacting a non-gaseous patient sample with a selective barrier, wherein the selective barrier is permeable to carbon dioxide and substantially impermeable to water; and contacting a carbon dioxide-containing portion of the patient sample with a solid indicator layer, wherein the indicator is adapted to provide feedback related to a presence of carbon dioxide.

There is also provided a method of manufacturing a sensor that includes: providing a solid indicator layer adapted to provide feedback related to a presence of carbon dioxide in a non-gaseous patient sample; and providing a selective barrier disposed on a sample-contacting side of the indicator, wherein the selective barrier is permeable to carbon dioxide and substantially impermeable to water.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

Figure 1:
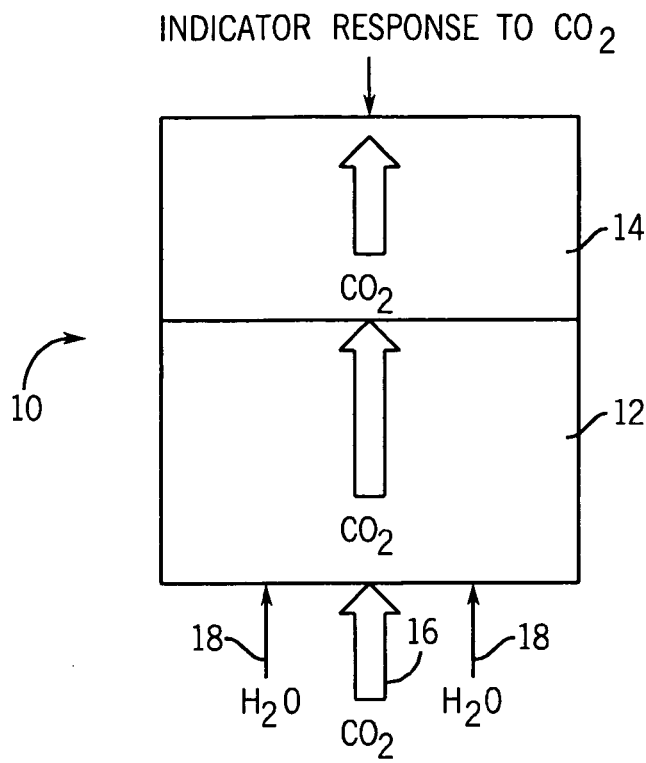
FIG. 1 is a schematic cross-section of a carbon dioxide sensor showing the selective barrier layer according to the present invention.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A sensor is provided herein that may assess carbon dioxide that perfuses through a barrier layer that is resistant to water but is permeable to carbon dioxide. Thus, such sensors are appropriate for use in an aqueous environment. Sensors according to the present techniques may transcutaneously sense carbon dioxide in a mucous membrane layer and/or carbon dioxide dissolved in patient fluids, such as salivary or mucosal fluids.

Carbon dioxide generated by metabolic activity occurring in the bloodstream may diffuse through the tissue and may dissolve into any liquids that may be found at the surface of the tissue. Thus, the levels of carbon dioxide in the tissue and bodily fluids may serve as a surrogate marker for carbon dioxide levels in the bloodstream. A sensor according to the present techniques placed adjacent to a tissue surface or a bodily fluid may capture carbon dioxide that would otherwise diffuse into the airstream or other surrounding airspace.

Generally, it is envisioned that a sensor according to the present technique is appropriate for use in determining the presence or levels of carbon dioxide in a variety of nongaseous patient sample sites, including tissue and/or bodily fluids. The sensor may be held against the mucosal tissue, either manually or otherwise, forming a seal to prevent the carbon dioxide from diffusing away. For example, a sensor may be used in the upper respiratory tract, including the oral and nasal passages. The oral passages may include the tongue, the floor of the mouth, the roof of the mouth, the soft palate, the cheeks, the gums, the lips, and any other oral tissue. Further, a sensor as described herein is appropriate for use adjacent to or proximate to any mucosal surface, i.e. patient surfaces that include a mucous membrane or surfaces that are associated with mucus production. In addition to the respiratory tract, mucosal surfaces may include vaginal or rectal surfaces.

Sensors as provided by the present techniques may be disposable or reusable. In addition, the sensors may be appropriate for short-term spot-checking or for longer-term, continuous monitoring. When used for long-term monitoring, the sensor may be applied to the patient's tissue by a suitable adhesive, such as a mucoadhesive, or by any other suitable holding device.

In additional to carbon dioxide monitoring, sensors as provided herein may be used to monitor oxygen, ethanol, metabolic trace gases such as acetone or anesthetic gases such as isoflurane, halothane, desflurane, sevoflurane and enflurane that may diffuse transcutaneously. Further, sensors as provided herein may be used to monitor tissue gases associated with an acute or chronic disease state. For example, such sensors may monitor hydrogen ions or bicarbonate ions in the tissue as a marker to assess the acidity of the blood. Variations from normal blood pH may be useful in assessing renal function.

FIG. 1 is a schematic view of an exemplary sensor 10. The sensor 10 has a selective barrier layer 12 and an indicator layer 14. When the sensor 10 is contacted with a tissue or fluid sensor site, carbon dioxide in the tissue and fluids, indicated by arrow 16, contacts the selective barrier layer 12, which is permeable to the carbon dioxide. The selective barrier is relatively impermeable to the water in or on the surface of the tissue, represented by arrows 18. Thus, the carbon dioxide is able to perfuse into the indicator layer 14, while the water at the sensor site is prevented from contacting the indicator layer 14. The indicator layer 14 is adapted to respond to the change in carbon dioxide concentration and to provide a feedback, as discussed in more detail below.

The selective barrier 12 may include materials that are hydrophobic or otherwise water-resistant, but that are permeable to carbon dioxide. In certain embodiments, it is envisioned that the ratio of water permeability to carbon dioxide permeability of the selective barrier may be less than 10, and in certain embodiments, the ratio may be less than 1. Suitable materials include polymers, such as polytetrafluorethylene (PTFE). Other suitable materials include microporous polymer films, such as those available from the Landec Corporation (Menlo Park, Calif.). Such microporous polymer films are formed from a polymer film base with a customizable crystalline polymeric coating that may be customized to be highly permeable to carbon dioxide and relatively impermeable to water.

The thickness of the selective barrier 12 may be modified in order to achieve the desired rate of carbon dioxide perfusion and indicator response time. Indicator response time may involve a change in indicator color or may involve an electrical signal. Generally, response times may be in the range of instantaneous to less than 5 minutes. In certain embodiments, the response time is in the range of 5 seconds to 5 minutes. Where a very rapid response is desired, a thin film of the selective barrier, for example less than 0.2 mm in thickness, may be used. In certain embodiments, when a slower response is desired, the selective barrier 12 may range from 0.2 mm to several millimeters in thickness. Additionally, the selective barrier 12 may be formed with small pores that increase the carbon dioxide permeability. The pores may range in size from 0.1 microns to 5 microns, depending on the desired response time. In one embodiment, the selective barrier 12 may be a relatively thin PTFE material such as plumber's tape (0.04 mm). In other embodiments, the selective barrier may be a PTFE material such as Gore-Tex® (W. L. Gore & Associates, Inc., Newark, Del.). Alternatively, the selective barrier 12 may be formed from a combination of appropriate materials, such as materials that are heat-sealed to one another. For example, the selective barrier 12 may include a PTFE layer with a pore size of 3 microns and a second PTFE layer with a pore size of 0.1 microns.

The indicator layer 14 includes the active ingredient of the indicating element, which provides the required response signal when exposed to a given concentration of carbon dioxide. The active ingredient may be any indicator that is sensitive to the presence of carbon dioxide and that is capable of being calibrated to give a response signal corresponding to a given predetermined concentration of carbon dioxide. For example, the signal may be visual, such as a change in color, or electrical.

Indicators which provide a color change in a presence of carbon dioxide include chromogenic pH-sensitive indicators and oxidation/reduction indicators. A chromogenic pH-sensitive indicator will provide a color change upon exposure to a given concentration of carbon dioxide in the presence of other ingredients of the element which provide the appropriate chemical conditions to induce the required color change. A chromogenic pH-sensitive indicator, which may be a compound or mixture of compounds, changes color when there is a change in pH in the surrounding medium. In certain embodiments, the indicator is used in combination with a suitable base which provides an alkaline solution. The hydroxyl ions or amine residues present in the alkaline solution react chemically with carbon dioxide to produce a carbonate, bicarbonate and/or carbamate moiety. The resulting reaction depletes the hydroxyl ion or amine at the interface and thus lowers the pH at the surface of the component impregnated with the indicating element. The lowering of the pH causes a color change in the indicator.

Chromogenic pH-sensitive indicators according to the present techniques include metacresol purple, thymol blue, cresol red, phenol red, xylenol blue, a 3:1 mixture of cresol red and thymol blue, bromthymol blue, neutral red, phenolphthalein, rosolic acid, alpha-naphtholphthalein and orange I. Examples of other indicators which may be used in the present invention include bromcresol purple, bromphenol red, p-nitrophenol, m-nitrophenol, curcumin, quinoline blue, thymolphthalein and mixtures thereof. Suitable bases include sodium carbonate, lithium hydroxide, sodium hydroxide, potassium hydroxide, potassium carbonate, sodium barbitol, tribasic sodium phosphate, dibasic sodium phosphate, potassium acetate, monoethanolamine, diethanolamine and piperidine. In certain embodiments, it may be appropriate to incorporate surfactants, antioxidants and ultraviolet stabilizers in the indicator composition.

In other embodiments, it is contemplated that the carbon dioxide indicator may be an electrical indicator. When the indicator is an electrical or electronic device, it may be an electrode or transistor which is adapted to detect and measure changes in the ambient chemical parameters induced by the presence of critical amounts of carbon dioxide. For example, optical fiber carbon dioxide sensors may be used to convert a change in a chemical indicator to a quantitative measurement of carbon dioxide in the sample. Generally, such sensors operate by directing light of a predetermined wavelength from an external source through the optical fiber to impinge the chemical indicator. The intensity of the emitted fluorescent light returning along the fiber is directly related to the concentration of carbon dioxide in the sample as a result of the pH-sensitive indicator material present at the fiber tip (i.e., the pH of the indicator solution is directly related to carbon dioxide concentration, as a result of carbonic acid formation). The emitted light is carried by the optical fiber to a device where it is detected and converted electronically to a carbon dioxide concentration value. The sensor may additionally have a reference dye present in the indicator composition. The intensity of the light emitted form the reference dye may be used to compensate, via rationing, the signal obtained from the indicator. In one embodiment, the electrical indicator may include nanoelectronic components, such as carbon nanotubes that are coated with a carbon dioxide-sensitive compound or polymer, such as a polyethyleneimine and starch polymer. Carbon dioxide may combine with primary and tertiary amines in the polymer coating to form carbamates. The chemical reaction lowers the pH of the polymer coating, altering charge transfer to the carbon nanotubes and resulting in an electrical signal.

The indicator layer 14 may be formed from any appropriate substrate. For example, the indicator layer 14 may be filter paper that may be soaked in, dipped in, or otherwise exposed to the appropriate carbon dioxide-sensing compounds. In certain embodiments, only one side of the filter paper may be dipped into a solution containing the indicating compounds. The indicator layer 14 may be formed from polysulfone, polypropylene, or other polymer substrates, for example. The indicator layer 14 may be a thin film or a thicker substrate. A thicker substrate may lead to a slower response time, which may be advantageous in situations in which a sensor is monitoring carbon dioxide levels over a longer period of time. Additionally, the indicator layer 14 may have pores of a variety of sizes. In certain embodiments, the pore sizes of the indicator layer 14 substrate range from 0.2 microns to 5 microns.

Generally, the indicator layer 14 may be attached to the selective barrier 12 by any suitable means, such as by adhesives, heat sealing, or lamination. In certain embodiments, the selective barrier 12 may encapsulate and substantially surround the indicator layer 14. Although regular water infiltration into an indicator layer may lead to damage and inaccurate measurements, certain carbon dioxide indicators may work best in the presence of a small amount of water that is typically provided when preparing the indicator layer 14. Thus, complete encapsulation of the indicator layer 14 may serve to provide the additional advantage of preventing or slowing the drying out of the small amount of water present in the indicator layer 14.

Figure 2:
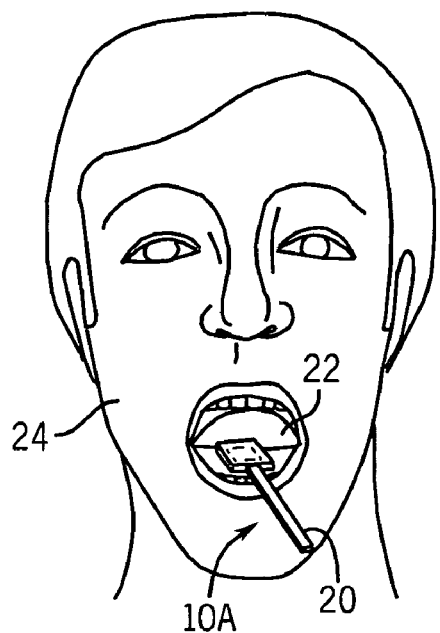
FIG. 2 illustrates a perspective view of a patient using a sensor for carbon dioxide detection according to the present invention.

In specific embodiments, it may be advantageous to provide a sensor assembly 10A as a dipstick-like device with a holder 20 that has a familiar and comfortable shape that is easy to use. For example, water-resistant sensors as provided herein may be used in vivo by a patient much like an oral thermometer. For example, FIG. 2 illustrates the placement of a sensor assembly 10A according to the present techniques adjacent a mucosal surface in the upper respiratory tract, such as a sublingual surface, in order to assess carbon dioxide in the tissue or oral liquids. The sensor assembly 10A includes a holder 20 that may be inserted into the oral passage and placed under the tongue 22 of the patient 24. The holder 20 may be suitably sized and shaped such that a patient may easily close his or her mouth around the holder 20 with minimal discomfort. In certain embodiments, the holder 20 may be adapted to be held against the cheek or any other mucosal tissue.

Figure 3:
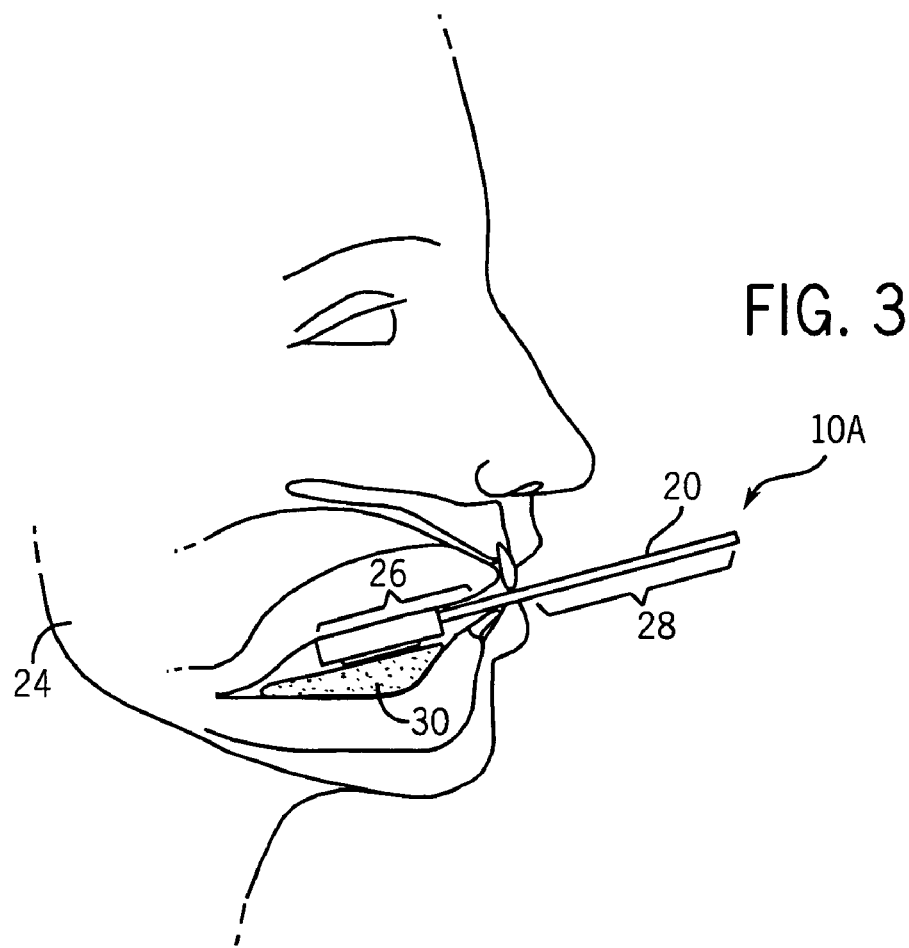
FIG. 3 illustrates a cross-sectional view of the patient's oral passage with a sensor for carbon dioxide detection applied under the patient's tongue according to the present invention.

FIG. 3 shows a cross-sectional view of the patient 24 with the sensor assembly 10A placed sublingually. The holder 20 has a sublingual portion 26 that is shaped to fit under the patient's tongue 22 and to lie on the floor of the mouth. The holder also has a handle portion 28 that is accessible from outside the mouth and may be manipulated by the patient 24 or a healthcare worker in order to properly position the sensor assembly 10A within the mouth. The holder 20 may contain an opening, such as a slot, that contains the sensing components (e.g. the selective barrier and indicator layer as described above) such that when the holder 20 is inserted into the mouth, the sensing components are positioned to be inside the mouth. In certain embodiments, the holder 20 may include electrical input and output wires (not shown) that may extend along the holder 20 to contact the sensing components.

The holder 20 may also serve to prevent air flow around the sensor, thus preventing carbon dioxide in the tissue or oral fluids 30 from dissipating into the airstream, which may lead to inaccurate measurements. Generally, the sublingual portion 26 of the holder 20 may be suitably sized and shaped to allow the sensor assembly 10A to be positioned flush against the tissue, trapping any oral fluids 30 between the tissue and the sensor assembly 10A. Thus, it is more likely that the dissolved carbon dioxide in the oral fluids 30 may contact the carbon dioxide sensing elements of the sensor assembly 10A.

Figure 4:
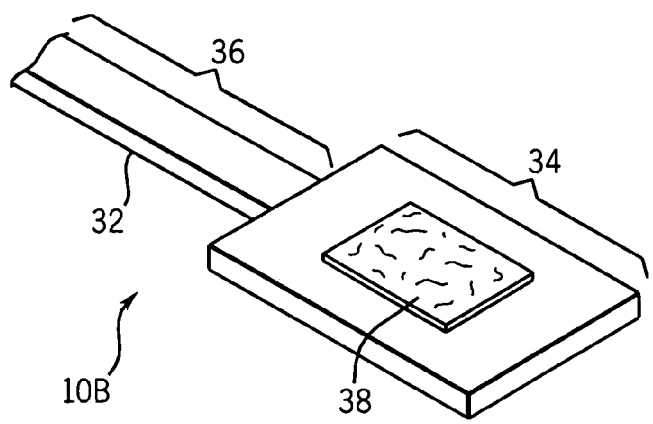
FIG. 4 illustrates a perspective view of an exemplary sensor for carbon dioxide detection.

FIG. 4 is a perspective view of a sensor assembly 10B with a holder 32, which includes a tissue-contacting portion 34 and a handle portion 36. The holder 32 may be formed of an elastomeric material, such as a soft rubber or soft foam or of a more rigid plastic material. The handle 34 extends outwardly from the tissue-contacting portion 36 and may include a flexible cable (not shown) that extends outwardly from the handle 34 and may provide a connection to a medical monitoring device. The cable may be detachable, such that the cable is reusable after the sensor assembly 10B is disposed of. As depicted, the sensor assembly 10B includes a transparent window 38 that allows viewing of the color change of the sensing elements.

Figure 5:
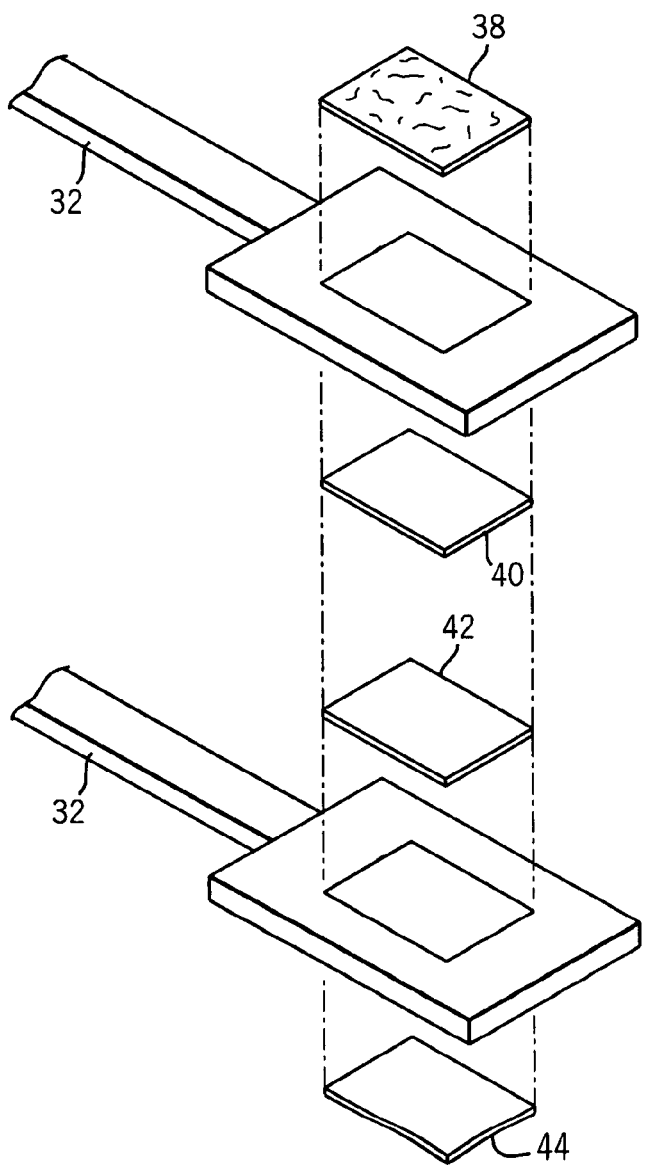
FIG. 5 illustrates an exploded view of an exemplary sensor for carbon dioxide detection.

FIG. 5 depicts an exploded view of the sensor assembly 10B. The sensor 10B includes a transparent window 38 disposed on a surface of an indicator layer 40. A selective barrier 42 is disposed on the indicator layer 40 on the opposite side from the transparent layer 38. A porous substrate 44 is disposed on the selective barrier layer. It is contemplated that the transparent window 38, the indicator layer 40, the selective barrier 42, and the porous substrate 44 may be attached to one another with adhesives or by a heat sealing process. In an alternate embodiment, the transparent window 38 and the porous substrate 44 may integrally formed with the holder 40.

The transparent window 38 may be any suitable optically transparent material that allows for viewing of the indicator layer 40 beneath. Exemplary materials include transparent polymers, such as polypropylene or polyethylene terephlate.

In certain embodiments, no transparent layer is used in conjunction with the sensor assembly 10B. For example, in embodiments in which the indicator provides an electrical signal that is received by a monitor, the sensor assembly 10B may not include a transparent layer.

The porous substrate 44 may be any suitable material which is permeable to carbon dioxide. As the indicator layer 40 and the selective barrier 42 may be quite thin, the porous substrate 44 may be advantageous in providing rigidity and support to the sensor assembly 10B. Suitable materials include paper, plastics, or woven materials. In certain embodiments, no porous substrate 44 is used in conjunction with the sensor assembly 10B.

Figure 6:
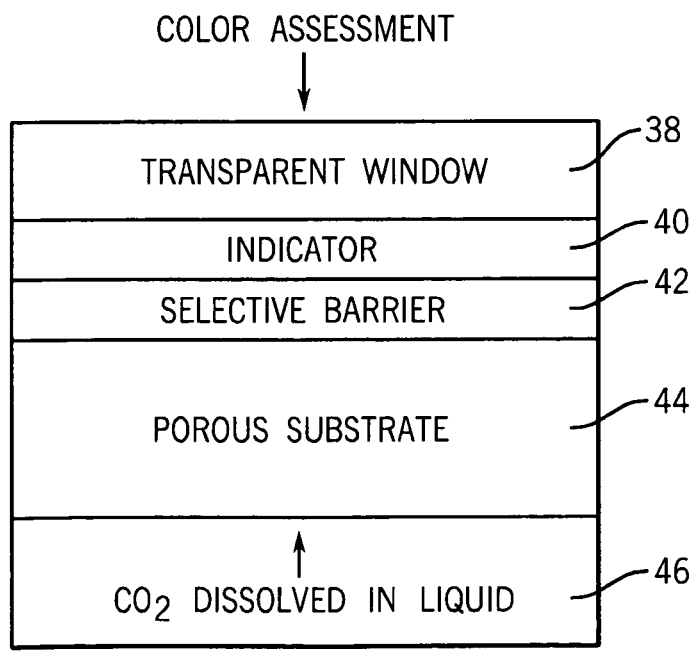
FIG. 6 is a schematic cross-section of the carbon dioxide sensor of FIG. 5 according to the present invention.

FIG. 6 is a schematic view of the sensor assembly 10B. Carbon dioxide 46 dissolved in liquid at the surface of the mucosal tissue contacts the porous substrate 44 when the sensor assembly 10B is applied to a mucosal surface. The porous substrate 44 is permeable to carbon dioxide 46, which diffuses through the selective barrier 42 to contact the indicator layer 40. The transparent window 38 allows viewing of the response, such as a change in color of the indicator layer 40. Water in the liquid sample may be able to diffuse through the porous substrate 44, but is repelled by the selective barrier 42, and thus prevented from reaching the indicator layer 40.

Figure 7:
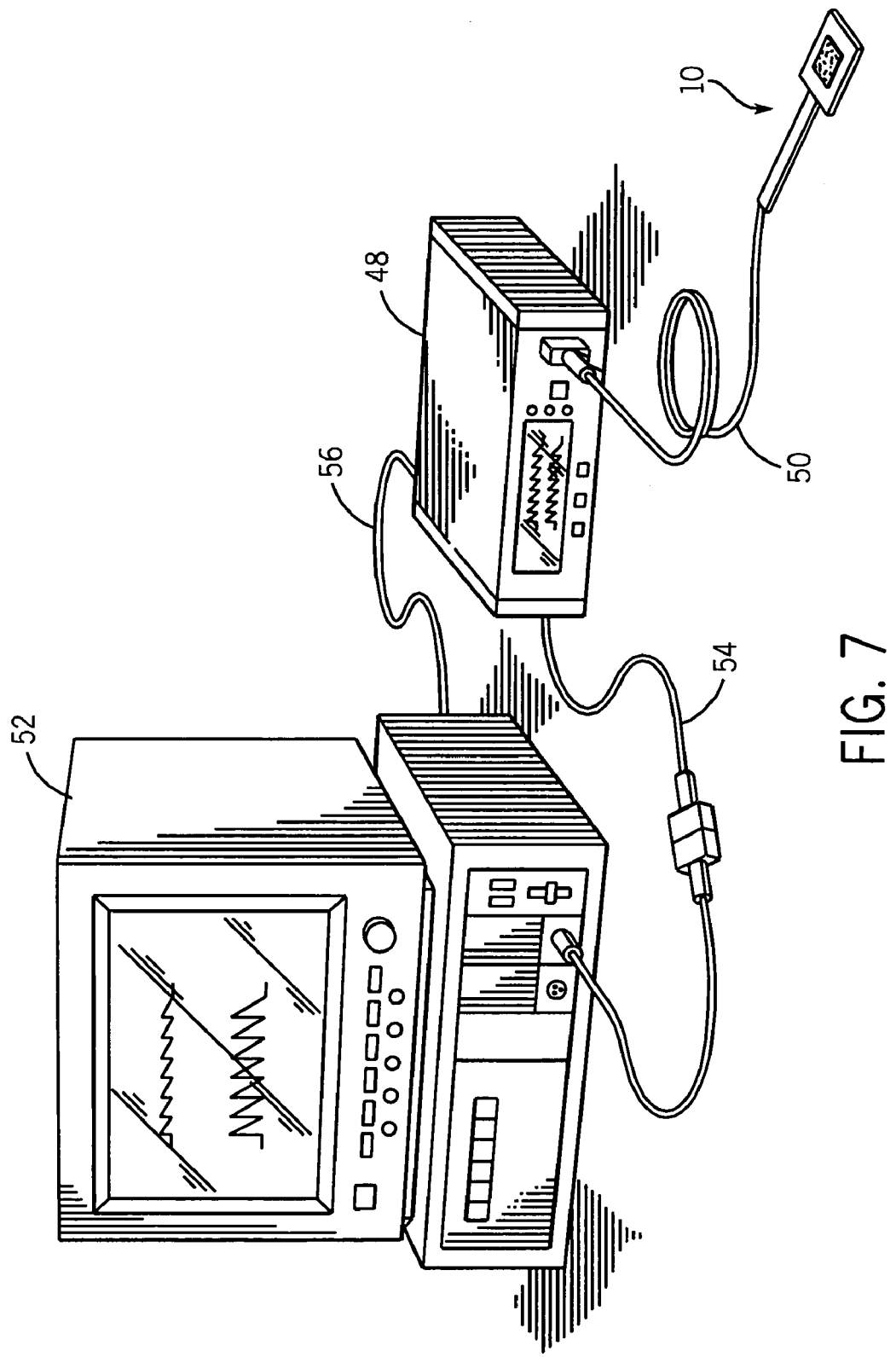
FIG. 7 illustrates a carbon dioxide detection system coupled to a multi-parameter patient monitor and a sensor according to embodiments of the present invention.

The exemplary sensors described herein, described here generically as a sensor 10, may be coupled to a monitor that may display the concentration of carbon dioxide in the patient sample (e.g. mucosal tissue or bodily fluids), as shown in FIG. 7. It should be appreciated that the cable 50 of the sensor 10 may be coupled to the monitor 48 or it may be coupled to a transmission device (not shown) to facilitate wireless transmission between the sensor 10 and the monitor 48. The monitor 48 may be any suitable carbon dioxide monitor, such as those available from Nellcor Puritan Bennett Inc. Furthermore, to upgrade conventional carbon dioxide detection provided by the monitor 48 to provide additional functions, the monitor 48 may be coupled to a multi-parameter patient monitor 52 via a cable 54 connected to a sensor input port or via a cable 56 connected to a digital communication port.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of carbon dioxide, but these techniques may also be utilized for the measurement and/or analysis of other blood constituents. Rather, the invention is to cover all modifications, equivalents, and alternatives falling within the spirit and scope of the invention as defined by the following appended claims. It will be appreciated by those working in the art that sensors fabricated using the presently disclosed and claimed techniques may be used in a wide variety of contexts. That is, while the invention has primarily been described in conjunction with the measurement of carbon dioxide concentration in blood, the sensors fabricated using the present method may be used to evaluate any number of sample types in a variety of industries, including fermentation technology, cell culture, and other biotechnology applications.

What is claimed is:

1. A sensor comprising:
   a porous substrate being permeable to water and carbon dioxide and having a first surface and a second surface, the first surface being adapted to be placed on mucosal tissue of a patient to obtain a sample;
   a selective barrier being permeable to carbon dioxide and substantially impermeable to water, the selective barrier being disposed on the second surface of the porous substrate; and
   a solid indicator disposed on the selective barrier opposite the porous substrate, the solid indicator being adapted to provide feedback related to a presence of carbon dioxide in a non-gaseous portion of the sample.

2. The sensor, as set forth in claim 1, wherein the selective barrier has a ratio of water permeability to carbon dioxide permeability of less than 10.

3. The sensor, as set forth in claim 1, comprising an optically transparent layer or an optically opaque layer disposed on the indicator opposite the selective barrier.

4. The sensor, as set forth in claim 1, comprising a holder adapted to hold the sensor adjacent to the mucosal tissue.

5. The sensor, as set forth in claim 1, wherein the indicator comprises a carbon dioxide-sensitive chemical compound.

6. The sensor, as set forth in claim 1, wherein the selective barrier comprises a polymer film.

7. The sensor, as set forth in claim 6, wherein the polymer film comprises pores less than 5 microns in diameter.

8. The sensor, as set forth in claim 1, wherein the selective barrier comprises a polytetrafluoroethylene layer.

9. A system comprising:
a monitor; and
a sensor adapted to be operatively coupled to the monitor, the sensor comprising:
- a porous substrate being permeable to water and carbon dioxide and having a first surface and a second surface, the first surface being adapted to be placed on mucosal tissue of a patient to obtain a sample;
- a selective barrier being permeable to carbon dioxide and substantially impermeable to water, the selective barrier being disposed on the second surface of the porous substrate; and
- a solid indicator disposed on the selective barrier opposite the porous substrate, the solid indicator being adapted to provide feedback related to a presence of carbon dioxide in a non-gaseous portion of the sample.

10. The system, as set forth in claim 9, wherein the selective barrier has a ratio of water permeability to carbon dioxide permeability of less than 10.

11. The system, as set forth in claim 9, comprising an optically transparent or an optically opaque layer disposed on the indicator opposite the selective barrier.

12. The system, as set forth in claim 9, comprising a holder adapted to hold the sensor adjacent to the mucosal tissue.

13. The system, as set forth in claim 9, wherein the indicator comprises a carbon dioxide-sensitive chemical compound.

14. The system, as set forth in claim 9, wherein the selective barrier comprises a polymer film.

15. The system, as set forth in claim 14, wherein the polymer film comprises pores less than 5 microns in diameter.

16. The system, as set forth in claim 9, wherein the selective barrier comprises a polytetrafluoroethylene layer.

17. A method comprising:
- taking a patient sample by contacting a mucosal tissue of a patient with a porous substrate that is permeable to water and carbon dioxide, wherein the porous substrate is disposed on a sample-contacting surface of a selective barrier;
- contacting the patient sample with the sample-contacting surface of the selective barrier, wherein the selective barrier is permeable to carbon dioxide and substantially impermeable to water; and
- contacting a carbon dioxide-containing portion of the patient sample with a solid indicator layer disposed on a surface of the selective barrier opposite the sample-contacting surface, wherein the indicator is adapted to provide feedback related to a presence of carbon dioxide.

18. The method, as set forth in claim 17, wherein the selective barrier has a ratio of water permeability to carbon dioxide permeability of less than 10.

19. The method, as set forth in claim 17, comprising assessing the presence of carbon dioxide by viewing the indicator through an optically transparent layer.

20. The method, as set forth in claim 17, wherein the indicator changes color in response to the presence of carbon dioxide.

21. A method of providing a sensor, comprising:
- providing a solid indicator layer adapted to provide feedback related to a presence of carbon dioxide in a non-gaseous patient sample;
- providing a selective barrier disposed on a sample-contacting side of the indicator, wherein the selective barrier is permeable to carbon dioxide and substantially impermeable to water; and
- providing a holder adapted to hold the selective barrier against and in direct contact with a mucosal tissue.

22. The method, as set forth in claim 21, comprising:
- providing an optically transparent layer or an optically opaque layer disposed on the indicator.

23. The method, as set forth in claim 21, wherein the selective barrier substantially surrounds the indicator.

24. The method, as set forth in claim 21, comprising:
- providing a porous substrate that is permeable to water and carbon dioxide, wherein the porous substrate is disposed on the sample-contacting surface of the selective barrier.

25. The method, as set forth in claim 21, wherein the indicator comprises a carbon dioxide-sensitive chemical compound.

26. The method, as set forth in claim 21, wherein the selective barrier comprises a polymer film.

27. The method, as set forth in claim 26, wherein the polymer film comprises pores less than 5 microns in diameter.

28. The method, as set forth in claim 21, wherein the selective barrier comprises a polytetrafluoroethylene layer.

29. The method, as set forth in claim 21, wherein the selective barrier has a ratio of water permeability to carbon dioxide permeability of less than 10.

* * * * *